US012779067B2

(12) United States Patent
Morrison

(10) Patent No.: US 12,779,067 B2
(45) Date of Patent: Nov. 3, 2026

(54) MEDICAL DEVICE STERILIZATION SYSTEM WITH PLASMA-BASED DETECTION OF RESIDUAL ALCOHOL

(71) Applicant: ASP GLOBAL MANUFACTURING GMBH, Schaffhausen (CH)

(72) Inventor: Todd Morrison, Dana Point, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 709 days.

(21) Appl. No.: 18/027,427

(22) PCT Filed: Sep. 27, 2021

(86) PCT No.: PCT/IB2021/000657
§ 371 (c)(1),
(2) Date: Mar. 21, 2023

(87) PCT Pub. No.: WO2022/069937
PCT Pub. Date: Apr. 7, 2022

(65) Prior Publication Data

US 2023/0330287 A1 Oct. 19, 2023

Related U.S. Application Data

(60) Provisional application No. 63/084,713, filed on Sep. 29, 2020.

(51) Int. Cl.
*A61L 2/14* (2006.01)
*A61L 2/24* (2006.01)
(Continued)

(52) U.S. Cl.
CPC .................. *A61L 2/14* (2013.01); *A61L 2/24* (2013.01); *A61L 2/28* (2013.01); *A61L 2103/15* (2026.01);
(Continued)

(58) Field of Classification Search
CPC ..... A61L 2/14; A61L 2/24; A61L 2/28; A61L 2202/122; A61L 2202/14; A61L 2202/24
See application file for complete search history.

(56) References Cited

U.S. PATENT DOCUMENTS 5,600,142 A 2/1997 Van Den Berg et al.
5,847,392 A 12/1998 Van Den Berg et al.
(Continued)

FOREIGN PATENT DOCUMENTS

CA 3089677 A1 * 3/2019 ............... H05H 1/46
CN 207 521 347 U 6/2018
(Continued)

OTHER PUBLICATIONS

International Search Report and Written Opinion for PCT/IB2021/000657 dated Mar. 18, 2023, 23 pages.
(Continued)

*Primary Examiner* — Regina M Yoo
(74) *Attorney, Agent, or Firm* — Lerner David LLP

(57) ABSTRACT

A method includes initiating a sterilization process with a sterilizing machine while a medical device is positioned in a sterilization chamber of the sterilizing machine. The method further includes monitoring one or more parameters (e.g., plasma power profile) of the sterilization process to detect whether alcohol is present on or in the medical device. Based on the monitoring, the method further includes determining whether alcohol is present on or in the medical device. If alcohol is determined to be present on or in the medical device, the method further includes initiating a routine to reduce or eliminate the alcohol on or in the medical device. If alcohol is not determined to be present on or in the medical device, the method further includes com-
(Continued)

pleting sterilization of the medical device. The medical device may include an endoscope such as a gastrointestinal endoscope.

19 Claims, 6 Drawing Sheets

(51) Int. Cl.
*A61L 2/28* (2006.01)
*A61L 103/15* (2026.01)

(52) U.S. Cl.
CPC ..... *A61L 2202/122* (2013.01); *A61L 2202/14* (2013.01)

(56) References Cited

U.S. PATENT DOCUMENTS

| | | | | |
|---|---|---|---|---|
| 5,882,590 | A * | 3/1999 | Stewart | A61L 2/28 422/108 |
| 6,447,719 | B1 | 9/2002 | Agamohamadi et al. | |
| 6,852,277 | B2 | 2/2005 | Platt et al. | |
| 6,852,279 | B2 | 2/2005 | Williams et al. | |
| 6,939,519 | B2 | 9/2005 | Agamohamadi et al. | |
| 7,095,501 | B2 | 8/2006 | Lambert et al. | |
| 9,522,202 | B1 * | 12/2016 | Ahiska | A61L 2/14 |
| 10,201,269 | B2 | 2/2019 | Yang et al. | |
| 10,328,170 | B2 | 6/2019 | Yang et al. | |
| 10,443,083 | B2 | 10/2019 | Eghbal et al. | |
| 10,561,753 | B2 | 2/2020 | Thompson et al. | |
| 10,596,287 | B2 | 3/2020 | Dang et al. | |
| 10,632,220 | B2 | 4/2020 | Fang et al. | |
| 10,668,180 | B2 | 6/2020 | Thompson et al. | |
| 10,702,619 | B2 | 7/2020 | Fang et al. | |
| 10,907,126 | B2 | 2/2021 | Amin | |
| 11,324,845 | B1 * | 5/2022 | Ricciardi | A61L 2/06 |
| 2002/0122744 | A1 | 9/2002 | Hui et al. | |
| 2009/0053101 | A1 | 2/2009 | Hanada et al. | |
| 2017/0182342 | A1 * | 6/2017 | Park | B01J 19/088 |
| 2017/0252473 | A1 | 9/2017 | Thompson et al. | |
| 2017/0332891 | A1 | 11/2017 | Yang et al. | |
| 2018/0000976 | A1 | 1/2018 | Nowruzi et al. | |
| 2020/0230279 | A1 | 7/2020 | Nowruzi et al. | |

FOREIGN PATENT DOCUMENTS

| | | | | |
|---|---|---|---|---|
| CN | 108 404 173 A | 8/2018 | |
| CN | 210 268 120 U | 4/2020 | |
| CN | 111544607 A | 8/2020 | |
| CN | 111568387 A * | 8/2020 | A61L 9/14 |
| EP | 0736764 B1 * | 5/2002 | A61L 2/24 |
| JP | 2006026233 A | 2/2006 | |
| JP | 2007190176 A | 8/2007 | |
| JP | 2018008051 A | 1/2018 | |
| KR | 19990006864 A | 1/1999 | |
| WO | WO-2019130223 A1 * | 7/2019 | A61L 2/14 |

OTHER PUBLICATIONS

Nerandzic, Michelle et al.; Efficacy of Flexible Endoscope Drying Using Novel Endoscope Test Articles that Allow Direct Visualization of the Internal Channel Systems, AJIC: American Journal of Infection Control, Elsevier, Amsterdam, NL, vol. 29, No. 5, Sep. 3, 2020 (Sep. 3, 2020), pp. 614-621, XP086548023, ISSN: 0196-6553, DOI: 10.1016/J.AJIC.2020.08.034 [retrieved on Sep. 3, 2020] pp. 614,620.

* cited by examiner

MEDICAL DEVICE STERILIZATION SYSTEM WITH PLASMA-BASED DETECTION OF RESIDUAL ALCOHOL

This application is a national entry under 35 U.S.C. § 371 of International Pat. App. No. PCT/IB2021/000657, entitled "Medical Device Sterilization System with Plasma-Based Detection of Residual Alcohol," filed Sep. 27, 2021, the disclosure of which is incorporated by reference herein, in its entirety. International Pat. App. No. PCT/IB2021/000657 claims priority to U.S. Provisional Pat. App. No. 63/084,713, entitled "Medical Device Sterilization System with Plasma-Based Detection of Residual Alcohol," filed Sep. 29, 2020, the disclosure of which is incorporated by reference herein, in its entirety.

BACKGROUND

Re-usable medical devices such as certain surgical instruments, endoscopes, etc., may be sterilized before re-use to minimize the likelihood that a contaminated device might be used on a patient. Various sterilization techniques may be employed, such as steam, hydrogen peroxide, and vapor phase sterilization, either with or without a gas plasma and ethylene oxide (EtO).

Sterilization of medical devices may be performed with an automated sterilization system such as a STERRAD® System by Advanced Sterilization Products of Irvine, California. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein, in its entirety; U.S. Pat. No. 6,852,279, entitled "Sterilization with Temperature-Controlled Diffusion Path," issued Feb. 8, 2005, the disclosure of which is incorporated by reference herein, in its entirety; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein, in its entirety; U.S. Pat. No. 6,447,719, entitled "Power System for Sterilization Systems Employing Low Frequency Plasma," issued Sep. 10, 2002, the disclosure of which is incorporated by reference herein, in its entirety; U.S. Pat. No. 10,561,753, entitled "Method of Sterilizing Medical Devices, Analyzing Biological Indicators, and Linking Medical Device Sterilization Equipment," issued Feb. 18, 2020, the disclosure of which is incorporated by reference herein, in its entirety; and U.S. Pub. No. 2020/0230279, entitled "Apparatus and Method for Sterilizing Endoscope," published Jul. 23, 2020, the disclosure of which is incorporated by reference herein, in its entirety. Each different medical device may require a different arrangement and sterilization process.

While a variety of systems and methods have been made and used for medical device sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Overview of Sterilization System

Figure 1:
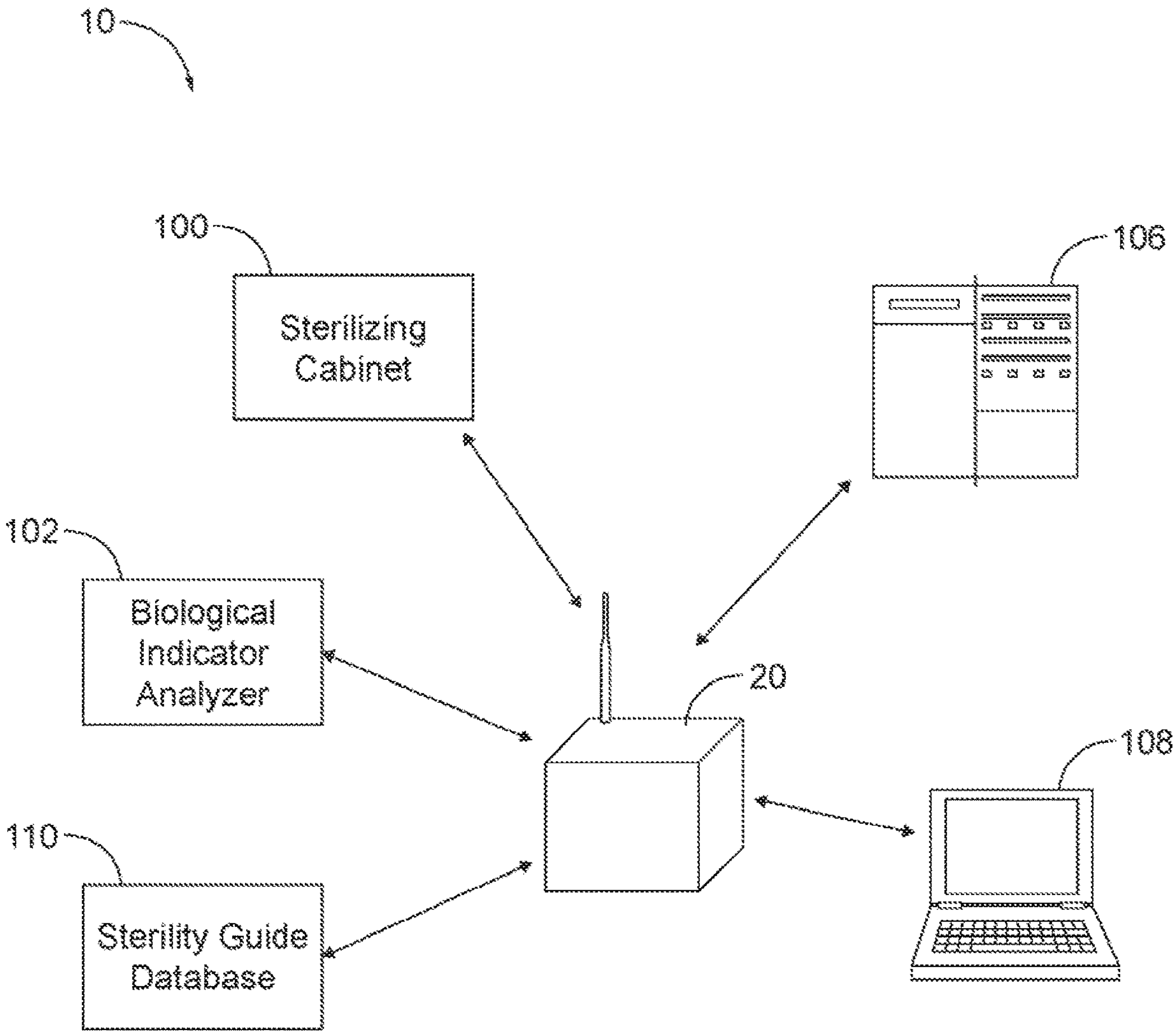
FIG. 1 depicts a schematic view of an example of a sterilization system.

FIG. 1 depicts a schematic view of an exemplary system (10) of interconnected devices that may be configured to perform methods associated with sterilizing medical devices (e.g., endoscopes and other medical devices). System (10) of this example includes a sterilizing cabinet (100), a biological indicator analyzer (102), a communication hub (20), a server (106), a user device (108), and a sterility guide database (110). Communication hub (20) is configured to provide transmission of data between sterilizing cabinet (100), biological indicator analyzer (102), communication hub (20), server (106), user device (108), and sterility guide database (110), as will be described in greater detail below.

Figure 2:
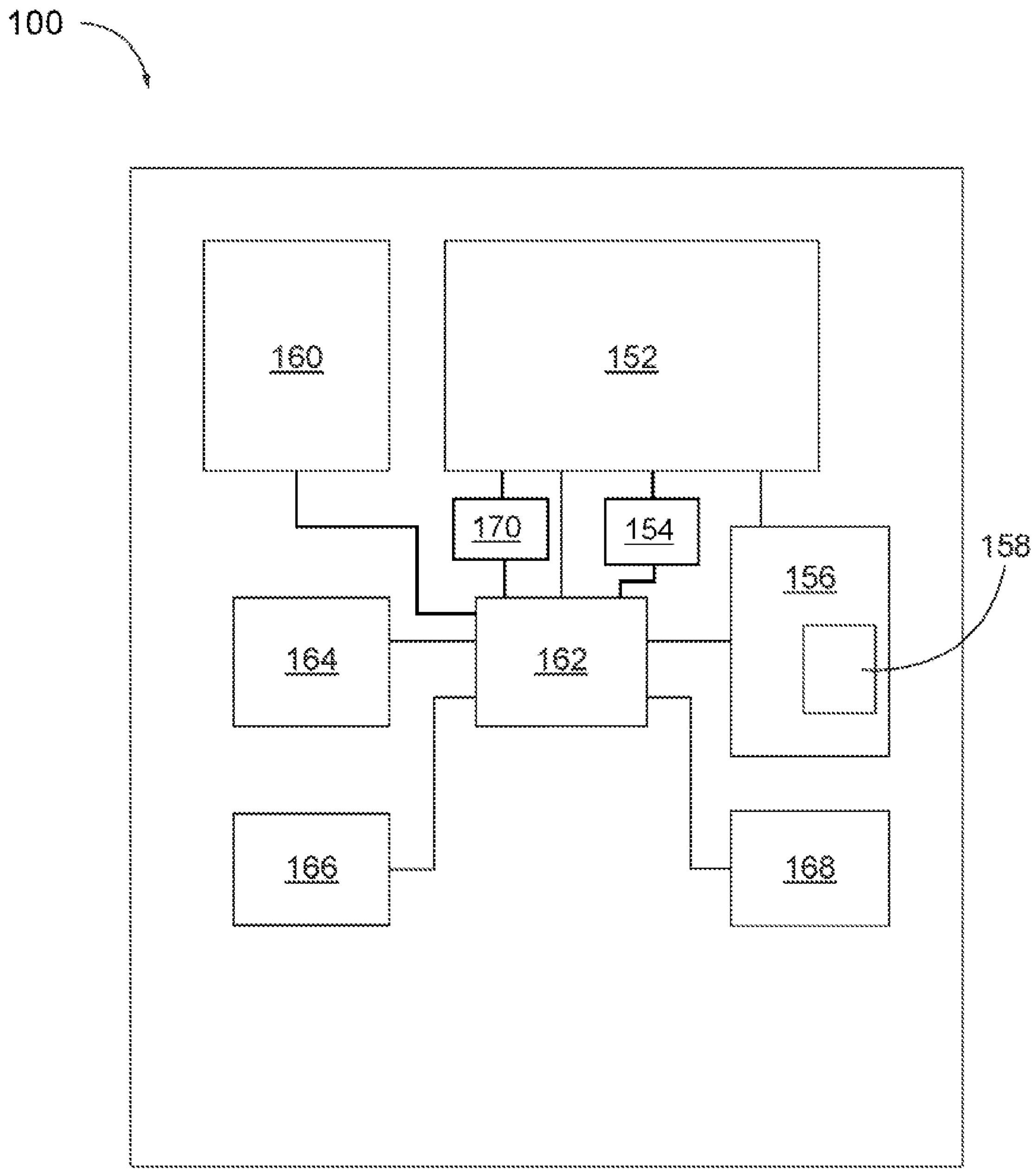
FIG. 2 depicts a schematic view of an example of a sterilizing cabinet that may be used with the system of FIG. 1.

FIG. 2 depicts an exemplary set of components that may be incorporated into sterilizing cabinet (100). Sterilizing cabinet (100) may be configured to perform one or more sterilization cycles, with different sterilization cycles being appropriate for different types and quantities of medical devices (e.g., endoscopes, etc.). Sterilizing cabinet (100) of the present example includes a sterilization chamber (152), which is configured to receive one or more medical devices for sterilization. Sterilizing cabinet (100) also includes a sterilization module (156) that is operable to receive sterilant cartridges (158) and dispense a sterilant from a cartridge (158) into sterilization chamber (152).

Sterilizing cabinet (100) further includes a touch screen display (160), which is operable to render various user interface display screens and receive user input in the form of the user contacting touch screen display (160). Sterilizing cabinet (100) may include various other kinds of user input features, including but not limited to buttons, keypads, keyboards, a mouse, a trackball, etc.

Sterilizing cabinet (100) of the present example further includes a processor (162), a communication module (164), a reader (166), and a memory (168). Processor (162) may include one or more microprocessors and/or various other kinds of hardware as will be apparent to those skilled in the art in view of the teachings herein. Processor (162) is in communication with the various components of sterilizing cabinet (100) and is operable to process data and execute control algorithms to drive various components of sterilizing cabinet (100). Communication module (164) is configured to enable bidirectional communication between sterilizing cabinet (100) and communication hub (20). Communication module (164) may also be configured to enable bidirectional communication between sterilizing cabinet (100) and server (106) and/or sterility guide database (110). Reader (166) is operable to read an identification tag of a biological indicator and/or other devices as described herein. Memory (168) is operable to store control logic and instructions and that are executed by processor (162) to drive components of sterilizing cabinet (100). Memory (168) may also be used to store results associated with setup of a sterilization cycle, performance of a load conditioning cycle, performance of a sterilization cycle, and/or various other kinds of information. Various suitable components and configurations that may be used to form processor (162), communication module (164), reader (166), and memory (168) will be apparent to those skilled in the art in view of the teachings herein.

Sterilizing cabinet (100) of the present example further includes a hydrogen peroxide sensor (154) that is in fluid communication with sterilization chamber (152), such that hydrogen peroxide sensor (154) is operable to detect levels of hydrogen peroxide within sterilization chamber (152). In some versions, hydrogen peroxide sensor (154) utilizes ultraviolet light to detect levels of hydrogen peroxide within sterilization chamber (152). Hydrogen peroxide sensor (154) is in electrical communication with processor (164), such that processor (164) may receive signals from hydrogen peroxide sensor (154) indicating levels of hydrogen peroxide within sterilization chamber (152). Processor (164) may automatically adjust parameters associated with sterilization cycles performed by sterilizing cabinet (100), and/or take other actions or refrain from taking certain actions, in response to real-time detected levels of hydrogen peroxide within sterilization chamber (152) as detected by hydrogen peroxide sensor (154).

Sterilizing cabinet (100) of the present example further includes a plasma generator (170) that is operable to generate a plasma within sterilization chamber (152). Plasma generator (170) is in electrical communication with processor (164), such that processor (164) is operable to drive plasma generator (170). Processor (164) may automatically adjust parameters associated with plasma generated by plasma generator (170). Such plasma related adjustments may be based on predetermined sterilization cycle routines as stored on memory (168). In addition, or in the alternative, such plasma related adjustment may be based on data that is being sensed in real time. By way of example only, processor (164) may adjust parameters associated with plasma generated by plasma generator (170) based at least in part on real-time data from hydrogen peroxide sensor (154). In addition to the foregoing, processor (164) may be configured to track data associated with the power profile driving plasma generator (170), such that processor (164) may track data associated directly with the plasma itself in real time. Processor (164) may further adjust parameters associated with plasma generated by plasma generator (170) based at least in part on real-time data from the power profile driving plasma generator (170).

In addition to the foregoing, sterilizing cabinet (100) may be configured and operable in accordance with at least some of the teachings of any of the patent references previously cited herein; U.S. Pat. No. 10,668,180, entitled "Apparatus and Method for Sterilizing Medical Devices," issued Jun. 2, 2020, the disclosure of which is incorporated by reference herein, in its entirety; and/or U.S. Pat. No. 10,561,753, entitled "Method of Sterilizing Medical Devices, Analyzing Biological Indicators, and Linking Medical Device Sterilization Equipment," issued Feb. 18, 2020, the disclosure of which is incorporated by reference herein, in its entirety.

In some cases, a biological indicator may be included in sterilizing cabinet (100, 150) along with the medical device during the sterilization process. The biological indicator may be activated before placement to cause a microorganism contained therein to multiply unless it is successfully sterilized during the procedure. After the sterilization process, the number of microorganisms present in the biological indicator may be determined by the biological indicator analyzer (102) to ensure that the sterilization process was successful for the biological indicator, which will also indicate that the sterilization procedure was successful for the medical device. Biological indicator analyzer (102) may receive a biological indicator and measure one or more characteristics of the biological indicator to gather data that may be used to determine whether the biological indicator tests positive, indicating that contamination is present after a sterilization procedure; or negative, indicating that no contamination is present after the sterilization procedure.

By way of example only, the biological indicator and biological indicator analyzer (102) may be configured and operable in accordance with at least some of the teachings of U.S. Pat. No. 10,907,126, entitled "Self-Contained Biological Indicator," issued Feb. 2, 2021, the disclosure of which is incorporated by reference herein, in its entirety; U.S. Pat. No. 10,443,083, entitled "Apparatus and Method for Analyzing Biological Indicators," issued Oct. 15, 2019, the disclosure of which is incorporated by reference herein, in its entirety; U.S. Pat. No. 10,561,753, entitled "Method of Sterilizing Medical Devices, Analyzing Biological Indicators, and Linking Medical Device Sterilization," issued Feb. 18, 2020, the disclosure of which is incorporated by reference herein, in its entirety; and/or U.S. Pat. No. 10,632,220, entitled "Biological Indicator with Variable Resistance," issued Apr. 28, 2020, the disclosure of which is incorporated by reference herein, in its entirety.

Server (106) may comprise a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also receive data from biological indicator analyzer (102) via communication hub (20).

User device (108) may comprise a device such as a laptop computer, a desktop computer, a mobile device such as a smartphone, tablet, or other mobile computing device; or a proprietary device having similar capabilities, such capabilities including wired or wireless communication with devices such as communication hub (20), a processor and memory, a display, a user interface, and other capabilities. User device (108) may be used to access and view information associated with one or more components (100, 102, 110, 106) of system (10) via communication hub (20); and may also be used to create or modify configurations and settings of communication hub (20) and connected devices. A user of user device (108) may view information and configure devices via, for example, a desktop software application, a mobile device software application, a web browser, or another software interface that may allow user device (108) to exchange information with communication hub (20). While only one user device (108) is shown in FIG. 1 as being in communication with communication hub (20), several user devices (108) may be in communication with communication hub (20). Similarly, several sterilizing cabinets (100), several biological indicator analyzers (102), several servers (106), and several sterility guide databases (110) may be in communication with communication hub (20).

Components (100, 102, 110, 106) of system (10) may each be coupled with communication hub (20) via any suitable wired and/or wireless communication technology, such as Ethernet, Wi-Fi, Bluetooth, USB, infrared, NFC, and/or other technologies. Communication hub (20) may relay data, etc., between components (100, 102, 110, 106) of system (10) as described herein, such that communication hub (20) serves as an intermediary. Various suitable components and configurations that may be used to form communication hub (20) will be apparent to those skilled in the art in view of the teachings herein. By way of example only, communication hub (20) and/or user device (108) may be configured and operable in accordance with at least some of the teachings of U.S. Pat. No. 10,596,287, entitled "Apparatus and Method to Link Medical Device Sterilization Equipment," issued Mar. 24, 2020, the disclosure of which is incorporated by reference herein, in its entirety; and/or U.S. Pat. No. 10,561,753, entitled "Method of Sterilizing Medical Devices, Analyzing Biological Indicators, and Linking Medical Device Sterilization Equipment," issued Feb. 18, 2020, the disclosure of which is incorporated by reference herein, in its entirety.

II. Overview of Sterilization Process

Figure 3:
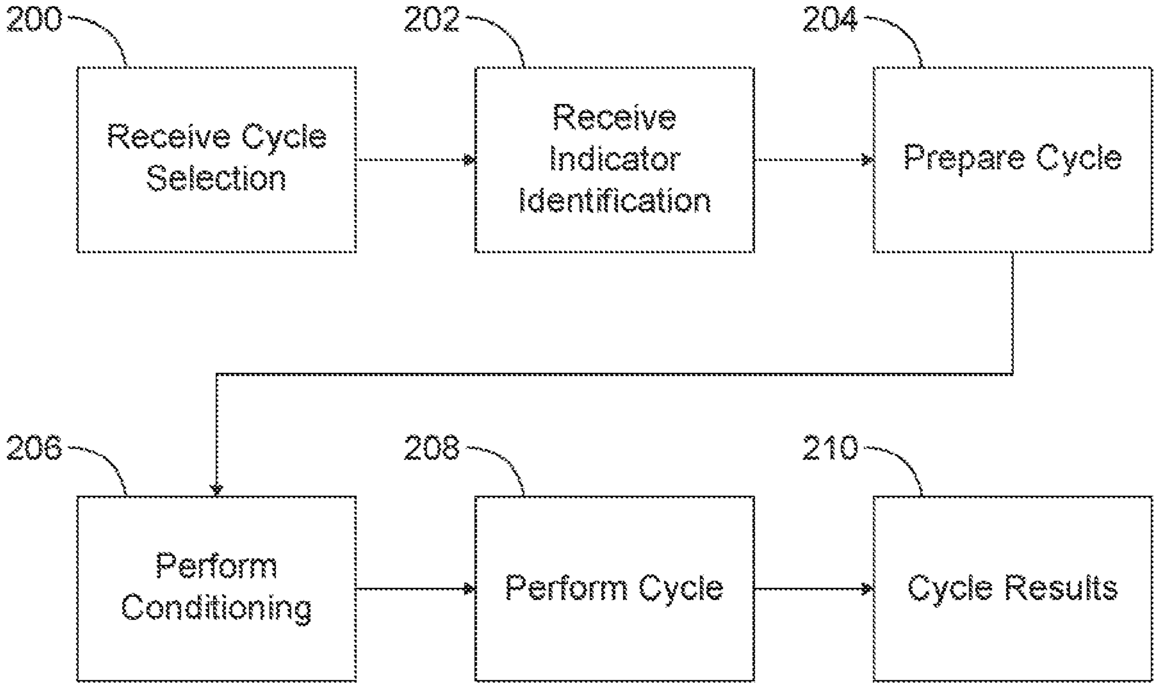
FIG. 3 depicts a flowchart of an example of a set of steps that the sterilizing cabinet of FIG. 2 may perform to sterilize a medical device.

FIG. 3 depicts an exemplary set of steps that system (10) could perform as a sterilization process to sterilize a medical device (e.g., endoscope, etc.). Initially, sterilizing cabinet (100) may display one or more sterilization cycles via touch screen display (160) and then receive a sterilization cycle selection (block 200) from the user. Sterilizing cabinet (100) may also display instructions indicating whether a biological indicator should be used with the selected sterilization cycle; and receive a biological indicator identification (block 202). A biological indicator may be placed inside sterilization chamber (152) before the sterilization cycle begins and may remain in sterilization chamber (152) during a sterilization cycle. The user may thus identify the particular biological indicator (block 202) before the biological indicator is placed the sterilization chamber (152).

Selection of a sterilization cycle (block 200) and identification of a biological indicator (block 202) may define one or more requirements for the configuration and arrangement of medical devices within sterilizing cabinet (100). A door of sterilization chamber (152) may be opened and instructions may be displayed to guide a user through preparation of the sterilization cycle (block 204), including placement of the biological indicator, placement of medical devices, closing the door of sterilization chamber (152), and/or other changes in preparation. Before initiating the actual sterilization cycle (block 208), sterilization cabinet (100) may also perform load conditioning (block 206) of the medical devices that are loaded in sterilization chamber (152). Such load conditioning (block 206) may include verifying that sterilization chamber (152) is sealed; verifying contents of sterilization chamber (152); checking physical characteristics of the contents of sterilization chamber (152) such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in sterilization chamber (152) for the sterilization cycle.

Once the load conditioning (block 206) has been completed, the selected sterilization cycle itself may be performed (block 208). The sterilization cycle (block 208) may include exposing the medical device(s) in sterilization chamber (152) to pressurized sterilant gas (e.g., hydrogen peroxide vapor, etc.), further heat treatment, chemical treatment, plasma treatment, vacuum treatment, and/or other types of sterilization procedures. After the sterilization cycle (block 208) is completed, the complete sterilization results may be displayed to a user via touch screen display (160); transmitted to server (106); printed locally; and/or displayed, transmitted, and/or stored via other devices as may be desirable. While block 208 is shown and described herein as a "sterilization cycle," the entire process shown in FIG. 3, including all steps of the process (blocks 200, 202, 204, 206, 208, 210) may be generally understood as a "sterilization process."

Sterilization cabinet (100) may also provide results (block 210) of the sterilization cycle. This provision of results (block 210) may include results from analysis of a biological indicator via biological indicator analyzer (102). These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history to determine if other past cycles may be the cause of the contamination; and/or if subsequently sterilized medical devices may need to be re-sterilized.

III. Detecting and Addressing Residual Alcohol on or in Medical Device in Sterilization System In some cases, a medical device that is to be sterilized within sterilization chamber (152) may be subject to a reprocessing stage before being placed in sterilization chamber (152). This reprocessing stage may include placement of the medical device in a reprocessing system, where the medical device is washed and disinfected. By way of example only, such reprocessing may be carried out in accordance with at least some of the teachings of U.S. Pub. No. 2017/0332891, entitled "Apparatus and method to Identify Endoscope Type and Provide Tailored Reprocessing," published Nov. 23, 2017, now abandoned, the disclosure of which is incorporated by reference herein, in its entirety; U.S. Pat. No. 10,201,269, entitled "Apparatus and Method for Reprocessing a Medical Device," issued Feb. 12, 2019, the disclosure of which is incorporated by reference herein, in its entirety; U.S. Pat. No. 10,328,170, entitled "Dynamic Disinfectant Dosage with Concentrate Degradation Compensation," issued Jun. 25, 2019, the disclosure of which is incorporated by reference herein, in its entirety; and/or U.S. Pat. No. 10,702,619, entitled "Apparatus and Method to Measure Concentration of Disinfectant in Medical Device Reprocessing System," issued Jul. 7, 2020, the disclosure of which is incorporated by reference herein, in its entirety.

Figure 4:
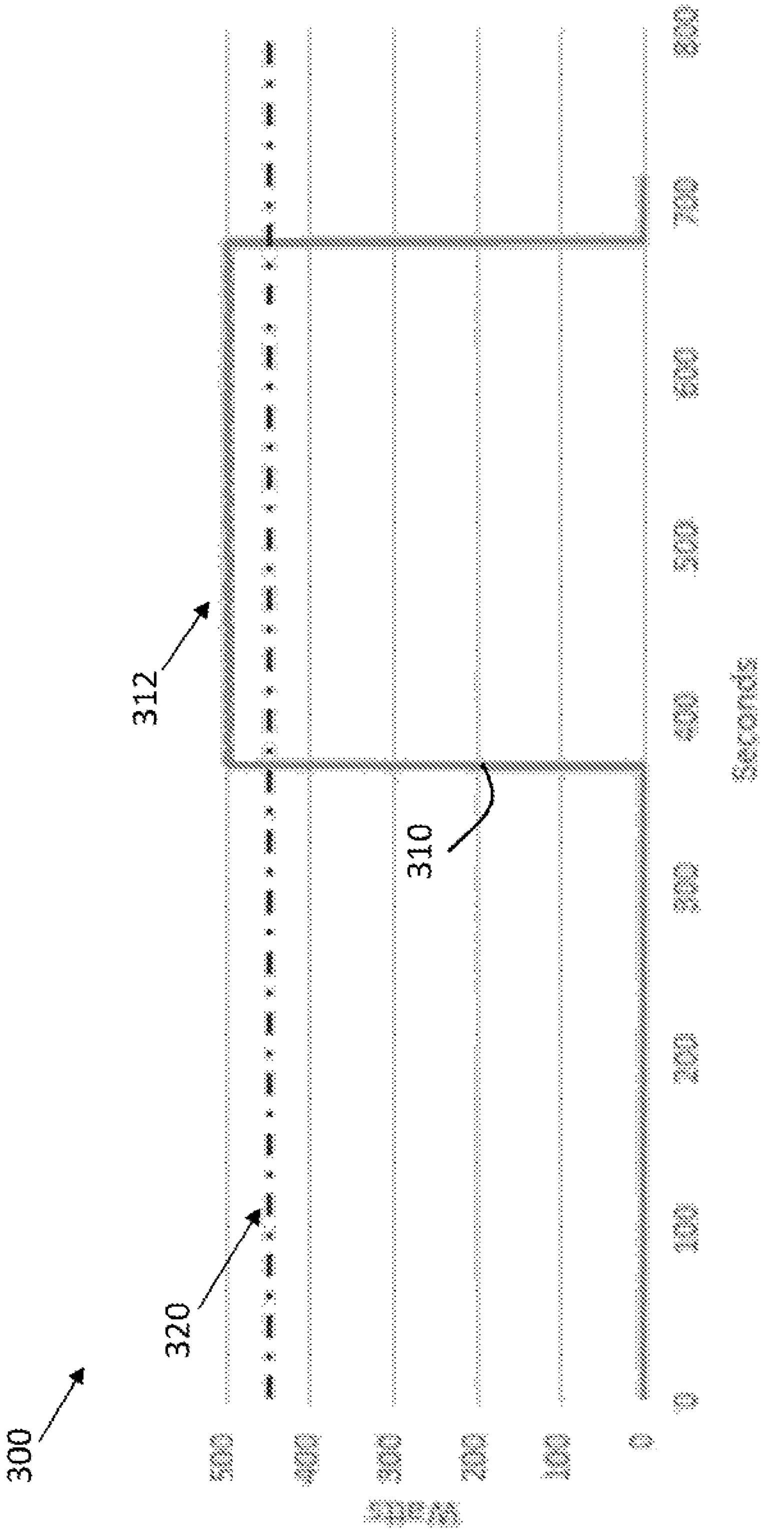
FIG. 4 depicts a graph showing an example of a plasma power profile during a sterilization cycle in the absence of residual alcohol in the medical device being sterilized.

As part of the reprocessing stage, a medical device may be exposed to alcohol (e.g., isopropyl alcohol) as a disinfectant and/or to aid in drying the medical device. In some instances, there may be some residual alcohol remaining on or in the medical device. In the context of endoscopes (e.g., gastrointestinal endoscopes), some such residual alcohol may remain within one or more working channels in the endoscope. Placing a medical device with residual alcohol in sterilization chamber (152), and then activating the sterilization process with the residual alcohol still remaining on or in the medical device, may lead to undesirable consequences. For instance, the presence of alcohol in sterilization chamber (152) during the sterilization process may lead to instability of plasma generated by plasma generator (170). For instance, FIG. 4 depicts a graph (300) showing a plot (310) of the power profile associated with plasma generated in sterilization chamber (152) by plasma generator (170), such as during load conditioning (block 206) or during a sterilization cycle (block 208), when the medical device in sterilization chamber (152) does not have residual alcohol. As shown, the power delivered to plasma generator (170) maintains a steady value of approximately 500 watts during a region (312) of plot (310) where the power achieves a lower threshold (320) associated with generation of plasma. By way of example only, an acceptable plasma power range may span from approximately 450 watts to approximately 550 watts, such that threshold (320) may be approximately 450 watts.

Figure 5:
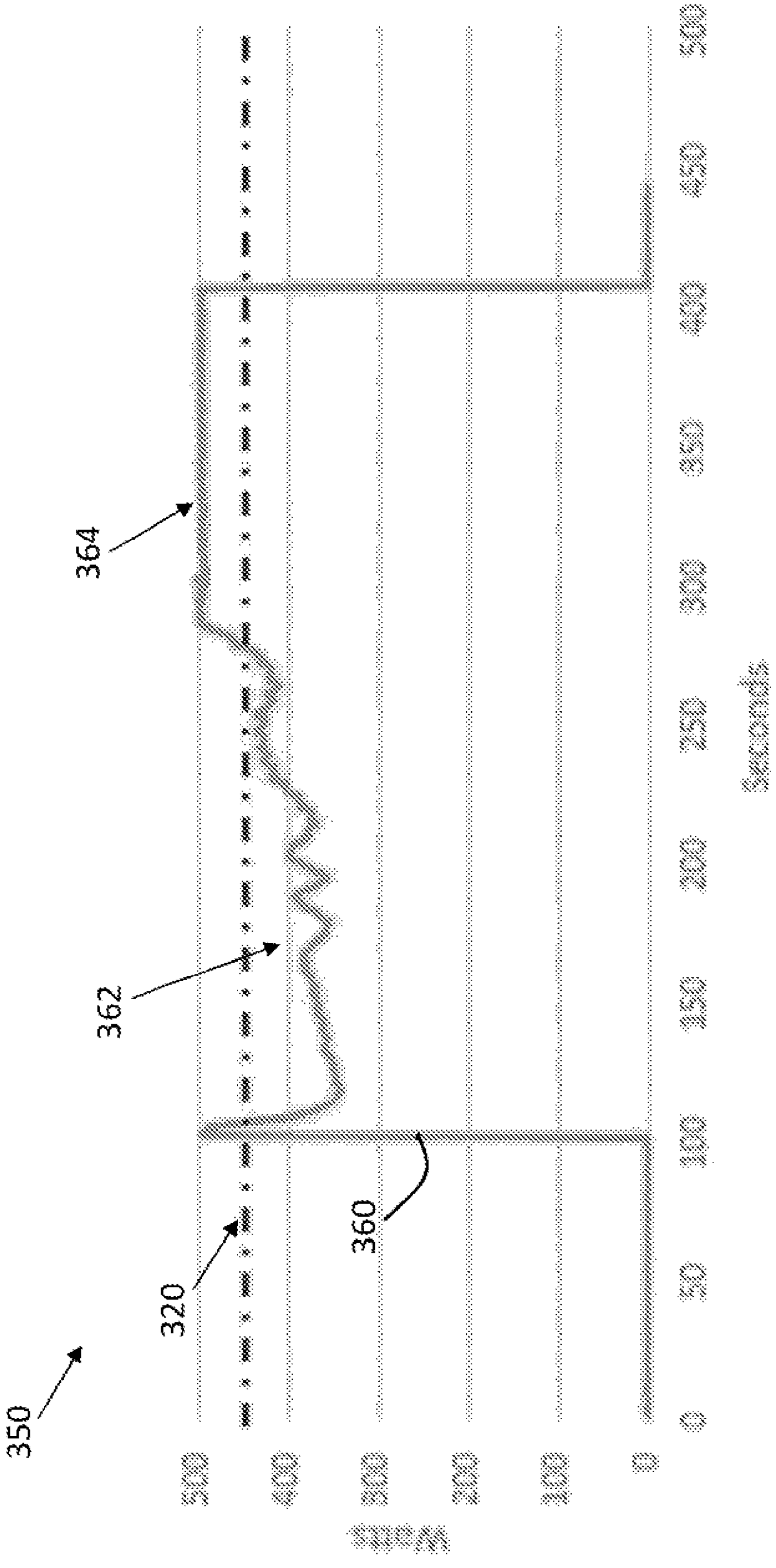
FIG. 5 depicts a graph showing an example of a plasma power profile during a sterilization cycle where residual alcohol is present on or in the medical device being sterilized.

By contrast, FIG. 5 depicts a graph (350) showing a plot (360) of the power profile associated with plasma generated in sterilization chamber (152) by plasma generator (170), such as during load conditioning (block 206) or during a sterilization cycle (block 208), when the medical device in sterilization (152) has some amount of residual alcohol. As shown, the power delivered to plasma generator (170) becomes erratic during a first region (362) of plot (360) where the power has achieved the lower threshold (320) associated with generation of plasma, even dropping below 450 watts (which, as noted above, may represent a minimum power level for generating plasma), though the power eventually achieves a steady value of approximately 500 watts during a second region (364) of plot (360) where the power achieves the lower threshold (320) associated with generation of plasma. The power delivered to plasma generator (170) may be erratic during first region (362) of plot (360) due to the presence of alcohol affecting the impedance at the electrode (not shown) of plasma generator (170). Despite the eventual achievement of a steady value in the plasma power profile, it may be desirable to avoid the erratic stage of such a power profile, to thereby achieve the profile associated with graph (300) on a consistent basis. While plot (360) shows the power level achieved the lower threshold (320) associated with generation of plasma before becoming erratic, there may be scenarios where the plasma power profile becomes erratic before reaching the lower threshold (320) associated with generation of plasma.

In addition, or in the alternative, the presence of alcohol on or in a medical device during the sterilization process may lead to premature degradation of the medical device that is being sterilized in sterilization chamber (152). In addition, or in the alternative, the presence of alcohol in sterilization chamber (152) during the sterilization process may impair the efficacy of the sterilization process. In addition, or in the alternative, the presence of alcohol in sterilization chamber (152) during the sterilization process may create safety risks during subsequent use of the medical device. For at least the foregoing reasons, it may be desirable to provide a version of sterilizing cabinet (100), and a method of operating sterilizing cabinet (100), where it is possible to detect the presence of alcohol in sterilization chamber (152) before the sterilization process is initiated or completed. Similarly, it may be desirable to provide a version of sterilizing cabinet (100), and a method of operating sterilizing cabinet (100), where it is possible to eliminate any alcohol that is detected in sterilization chamber (152) before the sterilization process is initiated or completed.

Figure 6:
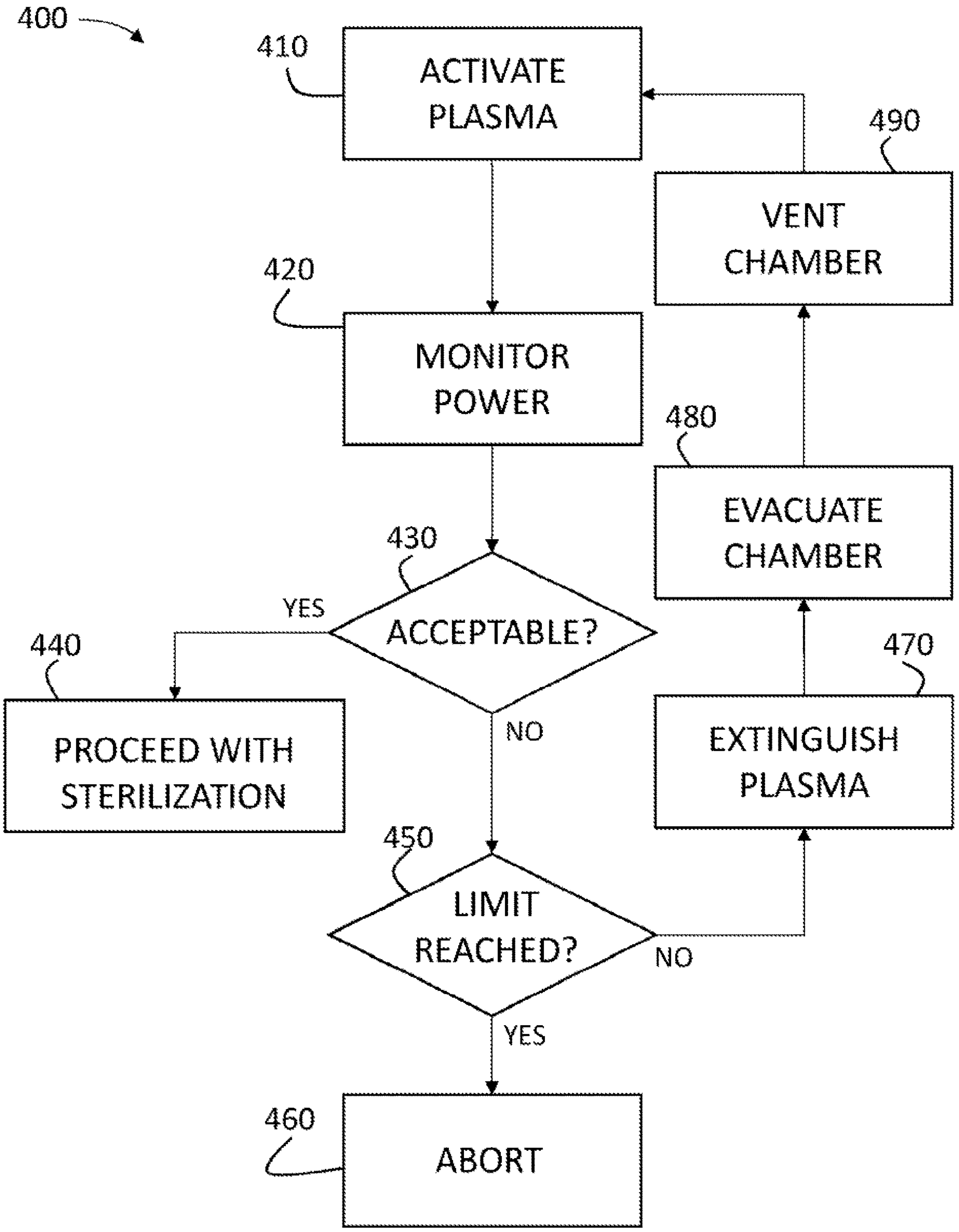
FIG. 6 depicts a flowchart of an example of a set of steps that may be performed to detect and address the presence of residual alcohol on or in a medical device in the sterilizing cabinet of FIG. 2.

As noted above in the comparison of graphs (300, 350) of FIGS. 5-6, the presence of alcohol on or in a medical device in sterilization chamber (152) may affect the power profile associated with plasma generated in sterilization chamber (152) by plasma generator (170). Thus, the power profile associated with plasma generated in sterilization chamber (152) may be monitored to detect the presence of alcohol in sterilization chamber (152). Such monitoring may be executed by processor (162) and/or any other suitable hardware components of sterilizing cabinet (100) as will be apparent to those skilled in the art in view of the teachings herein. FIG. 6 depicts a method (400) through which such monitoring may be carried out. By way of example only, method (400) may be carried out as part of load conditioning stage (block 206), as part of sterilization cycle (block 208), and/or at any other suitable time. By way of further example only, method (400) may be carried out before load conditioning stage (block 206).

As shown in FIG. 6, method (400) begins with activation of plasma (block 410) via plasma generator (170). As power is delivered to plasma generator (170), the power profile is monitored (block 420) to determine whether the power remains steady after crossing the threshold (320) associated with generation of plasma (e.g., as shown in region (312) of plot (310) in FIG. 4); or whether the power becomes erratic after crossing the threshold (320) associated with generation of plasma (e.g., as shown in region (362) of plot (360) FIG. 5). As noted above, such monitoring (block 420) may be carried out by processor (162). If processor (162) determines (block 430) that the power profile is acceptable, then method (400) may proceed (block 440) with the normal sterilization routine. In the event that method (400) is performed before, or as part of, load conditioning (block 206), sterilizing cabinet (100) may proceed (block 440) with load conditioning (block 206) at this point. In the event that method (400) is performed between load conditioning (block 206) and the sterilization cycle (block 208), sterilizing cabinet (100) may proceed (block 440) with sterilization cycle (block 208) at this point. Alternatively, sterilizing cabinet (100) may proceed (block 440) with whatever other stage of a sterilization routine might follow method (400) as will be apparent to those skilled in the art in view of the teachings herein.

In the event that processor (162) determines (block 430) that the plasma power profile is not acceptable, such that the power profile test (block 430) has been failed, then processor (162) may determine (block 450) whether a failure limit has been reached. As described below, sterilizing cabinet (100) may iterate through a routine in an attempt to eliminate the residual alcohol on or in the medical device in sterilization chamber (152), though it may be desirable to place a limit on how many such iterations may be performed before the process is aborted (block 460). In some versions, method (400) is configured such that up to four failures of the power profile test (block 430) may be tolerated; but five or more failures are unacceptable. Alternatively, any other suitable failure limit may be used. Regardless of which failure limit is used, method (400) may abort (block 460) in the event that the failure limit has been reached. In the event that method (400) is aborted (block 460), processor (162) may drive touch screen display (160) to inform the operator that residual alcohol has been detected and cannot be removed; and to further instruct the operator to retrieve the medical device from sterilization chamber (152) and run the medical device back through the reprocessing system before re-introducing the medical device to sterilization chamber (152). Alternatively, the operator may be prompted to take any other suitable action in the event that method (400) is aborted (block 460).

In the event that processor (162) determines (block 430) that the plasma power profile is not acceptable, and further determines (block 450) that the failure limit has not yet been reached, processor (162) may drive touch screen display (160) to inform the operator that residual alcohol has been detected, and that sterilizing cabinet (100) will attempt to remove the residual alcohol (e.g., via load conditioning block (206)). Processor (162) may further extinguish the plasma (block 470) by deactivating plasma generator (170). Processor (162) may then evacuate sterilization chamber (152) (block 480). By way of example only, sterilization chamber (152) may be vented to atmosphere as part of a process to evacuate sterilization chamber (152) (block 480). In addition, or in the alternative, a vacuum may be applied to sterilization chamber (152) to evacuate sterilization chamber (152) (block 480). By way of example only, sterilization chamber (152) may be actively evacuated (e.g., via vacuum pump) for approximately one minute.

Once sterilization chamber (152) has been sufficiently evacuated (block 480), the method (400) may be re-initiated through another iteration by activating plasma (block 410) in sterilization chamber (152). In order to achieve plasma re-activation (block 410), sterilization chamber (152) may first be vented (block 490) to achieve a plasma ignition pressure of approximately 500 mT, followed by activation of plasma generator (170) to light the plasma (block 410).

In some cases, this process of extinguishing the plasma (block 470), evacuating sterilization chamber (152) (block 480), and re-activating plasma (block 410) may reduce or eliminate the residual alcohol that is on or in the medical device in sterilization chamber (152). In some variations, method (400) may include additional steps as part of the process to remove residual alcohol from the medical device. For instance, sterilizing cabinet (100) may circulate warm, dry air through sterilization chamber (152) and over the medical device for a predetermined period. In addition, or in the alternative, method (400) may provide repeated steps of evacuating (block 480) sterilization chamber (152) and venting (block 490) sterilization chamber (152), in a pulsed fashion, before re-activating plasma (block 410). In addition, or in the alternative, method (400) may provide venting of sterilization chamber (152) to atmosphere, then holding the pressure in sterilization chamber (152) at atmosphere for a predetermined period, to allow for warm air convection within sterilization chamber (152); followed by evacuation of sterilization chamber (152) to remove vaporized alcohol. In addition, or in the alternative, method (400) may provide maintenance of a fixed pressure (e.g., approximately 500 mT) in sterilization chamber (152) for a predetermined period of time. Similarly, method (400) may isolate sterilization chamber (152) at a fixed pressure and monitor a rise in pressure in sterilization chamber (152) to determine if moisture has been removed of if moisture is still present within sterilization chamber (152) (e.g., as influenced by the presence of moisture on or in the medical device in sterilization chamber (152)). Alternatively, any other steps may be taken to address the presence of residual alcohol on or in the medical device in sterilization chamber (152), in addition to or as an alternative to the various steps described above.

In some scenarios where steps have been taken in an attempt to remove residual alcohol, method (400) may provide a longer duration of re-activated plasma (block 410) in second or subsequent iterations of method (400). This longer duration of re-activated plasma (block 410) may be calculated to compensate for time spent during the steps of extinguishing the plasma (block 470), evacuating (block 480), and venting (block 490) (as well as any other steps that may have been taken in an attempt to remove residual alcohol). In other words, processor (162) may integrate the plasma power curve vs. time to ensure that the total required power has been delivered as may be expected in a load conditioning (block 206) or sterilization cycle (block 208) in cases where no residual alcohol is present in the medical device.

As noted above, method (400) may be reiterated until either the failure limit has been reached (due to persistent residual alcohol) or the plasma power profile has been found to be acceptable (due to the eventual absence of residual alcohol).

In some variations of method (400), it may be determined in the first iteration that there is simply too much residual alcohol within sterilization chamber (152) (due to the presence of excessive residual alcohol on or in the medical device within sterilization chamber (152)), such that the sterilization process should be aborted without even attempting the iterations described above to remove the residual alcohol. By way of example only, processor (162) may determine that the amount of residual alcohol is "excessive" if two or more conditions are met. One such condition may include the erratic plasma power profile described above with reference to FIG. 5. Another such condition may include an excessively long sterilization chamber (152) evacuation time to achieve a target plasma pressure (e.g., approximately 500 mT). Examples of suitable thresholds of time to determine whether such time is "excessive" will be apparent to those skilled in the art in view of the teachings herein. If both such conditions are found in the same cycle, processor (162) may determine that the amount of residual alcohol is "excessive;" and may abort the sterilization process without attempting the iterations described above to remove the residual alcohol.

In some variations of method (400) certain other parameters may be monitored, in addition to or as an alternative to monitoring the plasma power, to determine whether residual alcohol is on or in the medical device in sterilization chamber (152). By way of example only, in versions where hydrogen peroxide vapor is used as a sterilant during sterilization cycle (block 208), processor (162) may track signals from hydrogen peroxide sensor (154) to determine whether the hydrogen peroxide degradation follows an expected curve or whether the hydrogen peroxide vapor degrades at a rate that deviates from the expected degradation curve. When alcohol is present on or in the medical device in sterilization chamber (152), the hydrogen peroxide vapor in sterilization chamber (152) may degrade faster than would otherwise be expected. Thus, substantial deviations from the expected curve of hydrogen peroxide degradation may indicate the presence of alcohol on or in the medical device in sterilization chamber (152). Processor (162) may factor such real time data from hydrogen peroxide sensor (154) into a variation of method (400). By way of example only, real time data from hydrogen peroxide sensor (154) may be analyzed in addition to, or in lieu of, the plasma power profile as part of the determination (block 430) of whether residual alcohol is present on or in the medical device in sterilization chamber (152).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method comprising: (a) initiating sterilization process with a sterilizing machine while a medical device is positioned in a sterilization chamber of the sterilizing machine; (b) monitoring one or more parameters of the sterilization process to detect whether alcohol is present on or in the medical device; (c) either: (i) determining, based on the monitoring, that alcohol is present on or in the medical device, or (ii) determining, based on the monitoring, that alcohol is not present on or in the medical device; and (d) either: (i) if alcohol is determined to be present on or in the medical device, initiating a routine to reduce or eliminate the alcohol on or in the medical device, (ii) if alcohol is not determined to be present on or in the medical device, completing sterilization of the medical device, or (iii) if a certain amount of alcohol is determined to be present on or in the medical device, aborting the sterilization process.

Example 2

The method of Example 1, the medical device comprising an endoscope.

Example 3

The method of Example 2, the endoscope comprising a gastrointestinal endoscope.

Example 4

The method of any of Examples 1 through 3, the sterilization process including a load conditioning cycle followed by a sterilization cycle.

Example 5

The method of Example 4, the load conditioning cycle including being configured to one or both of reduce moisture in the medical device or raise a temperature of the medical device.

Example 6

The method of any of Examples 4 through 5, the monitoring being performed during the load conditioning cycle.

Example 7

The method of any of Examples 4 through 6, the monitoring being performed during the sterilization cycle.

Example 8

The method of any of Examples 1 through 7, the sterilization process including applying a plasma to the sterilization chamber.

Example 9

The method of Example 8, the monitoring including monitoring a power profile associated with the plasma.

Example 10

The method of Example 9, wherein determining that alcohol is present includes determining that the power profile associated with the plasma becomes erratic before or after the power level reaches a threshold value associated with generation of a plasma.

Example 11

The method of Example 9, wherein determining that alcohol is not present includes determining that the power profile associated with the plasma remains stable after the power level reaches a threshold value associated with generation of a plasma.

Example 12

The method of any of Examples 8 through 11, the routine to reduce or eliminate the alcohol on or in the medical device including extinguishing the plasma.

Example 13

The method of any of Examples 11 through 12, the routine to reduce or eliminate the alcohol on or in the medical device including evacuating the sterilization chamber.

Example 14

The method of Example 13, wherein evacuating the sterilization chamber includes applying a vacuum to the sterilization chamber.

Example 15

The method of any of Examples 1 through 14, the sterilization process including delivering a hydrogen peroxide vapor to the sterilization chamber.

Example 16

The method of Example 15, the monitoring including monitoring a degradation curve associated with the hydrogen peroxide vapor.

Example 17

The method of Example 16, wherein determining that alcohol is present includes determining that a degradation rate of the hydrogen peroxide vapor exceeds an expected degradation curve.

Example 18

The method of any of Examples 1 through 17, the routine to reduce or eliminate the alcohol on or in the medical device including evacuating the sterilization chamber.

Example 19

The method of Example 18, wherein evacuating the sterilization chamber includes applying a vacuum to the sterilization chamber.

Example 20

The method of any of Examples 1 through 19, further comprising if alcohol is determined to be present on or in the medical device, performing a subsequent iteration of at least a portion of the sterilizing process again after initiating the routine to reduce or eliminate the alcohol on or in the medical device.

Example 21

The method of Example 20, further comprising monitoring one or more parameters of the sterilization process to detect whether alcohol is present on or in the medical device during the subsequent iteration.

Example 22

The method of Example 21, further comprising: (a) determining, based on the monitoring, that alcohol is still present on or in the medical device during the subsequent iteration; (b) determining whether a predetermined number of iterations of the at least a portion of the sterilizing process have been performed; and (c) either: (i) if the predetermined number of iterations have not been performed, initiating the routine to reduce or eliminate the alcohol on or in the medical device, or (ii) if the predetermined number of iterations have been performed, aborting the sterilization process.

Example 23

The method of Example 22, wherein aborting the sterilization process includes prompting an operator to remove the medical device from the sterilization chamber.

Example 24

The method of any of Examples 1 through 23, wherein the method is performed by a processor of the sterilizing machine.

Example 25

A method comprising: (a) generating a plasma in a sterilization chamber of the sterilizing machine while a medical device is positioned in the sterilization chamber; (b) monitoring a power profile associated with the plasma to detect whether alcohol is present on or in the medical device; and (c) using a processor to determine whether alcohol is present on or in the medical device, based on the monitored power profile.

Example 26

The method of Example 25, wherein using a processor to determine whether alcohol is present on or in the medical device results in a determination that alcohol is present on or in the medical device, the method further comprising initiating a routine to reduce or eliminate the alcohol on or in the medical device.

Example 27

The method of Example 26, the routine to reduce or eliminate the alcohol on or in the medical device including extinguishing the plasma.

Example 28

The method of any of Examples 26 through 27, the routine to reduce or eliminate the alcohol on or in the medical device including evacuating the sterilization chamber.

Example 29

The method of Example 25, wherein using a processor to determine whether alcohol is present on or in the medical device results in a determination that alcohol is not present on or in the medical device, the method further comprising completing sterilization of the medical device.

Example 30

The method of any of Examples 25 through 29, wherein using a processor to determine whether alcohol is present on or in the medical device, based on the monitored power profile, comprises determining whether the power profile associated with the plasma remains stable or becomes erratic before or after the power level reaches a threshold value associated with generation of a plasma.

Example 31

A system, comprising: (a) a sterilization chamber, the sterilization chamber being operable to receive a medical device; and (b) a processor, the processor being operable to drive a sterilization process on a medical device in the sterilization chamber, the processor being further configured to: (i) monitor one or more parameters of the sterilization process to detect whether alcohol is present on or in the medical device, (ii) determine, based on the monitoring, whether alcohol is present on or in the medical device, and (iii) based on whether alcohol is determined to be present on or in the medical device, either: (A) initiate a routine to reduce or eliminate the alcohol on or in the medical device, (B) complete sterilization of the medical device, or (C) if a certain amount of alcohol is determined to be present on or in the medical device, aborting the sterilization process.

Example 32

The system of Example 31, further comprising a plasma generator, the plasma generator being operable to generate a plasma in the sterilizing chamber.

Example 33

The system of Example 32, the processor being operable to drive the plasma generator.

Example 34

The system of any of Examples 32 through 33, the processor being further configured to monitor a power profile associated with driving of the plasma generator.

Example 35

The system of Example 34, the processor being configured to determine whether alcohol is present on or in the medical device based on behavior of the power profile before or after the power level reaches a threshold value associated with generation of a plasma.

Example 36

The system of Example 35, the processor being configured to determine that alcohol is present on or in the medical device based on the power profile becoming erratic before or after the power level reaches a threshold value associated with generation of a plasma.

Example 37

The system of any of Examples 35 through 36, the processor being configured to determine that alcohol is not present on or in the medical device based on the power profile remaining stable after the power level reaches a threshold value associated with generation of a plasma.

Example 38

The system of any of Examples 31 through 37, the processor being configured to extinguish the plasma as part of the routine to reduce or eliminate the alcohol on or in the medical device.

Example 39

The system of any of Examples 31 through 38, the processor being configured to evacuate the sterilizing chamber as part of the routine to reduce or eliminate the alcohol on or in the medical device.

Example 40

The system of Example 39, the processor being configured to trigger a vacuum in the sterilizing chamber to evacuate the sterilizing chamber as part of the routine to reduce or eliminate the alcohol on or in the medical device.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A system for sterilization, comprising:

a chamber operable to receive a device to be sterilized;

a processor operable to drive a sterilization process and further configured to:

detect, based on one or more parameters of the sterilization process, alcohol on or in the device; and in response to the alcohol being detected, run a routine to remove at least a part of the alcohol on or in the device; and a plasma generator, coupled to the processor, operable to generate a plasma in the chamber, wherein the one or more parameters comprise a plasma power profile associated with generating the plasma, and wherein the processor is further configured to:

detect the alcohol based on a characteristic of the plasma power profile associated with generating the plasma.

2. The system of claim 1, further comprising:

a hydrogen peroxide sensor, coupled to the processor, operable to detect levels of hydrogen peroxide within the chamber.

3. The system of claim 2, wherein the one or more parameters comprise a degradation rate of the hydrogen peroxide within the chamber, and wherein the processor is further configured to:

detect the alcohol based on a comparison of the degradation rate of the hydrogen peroxide within the chamber and an expected degradation curve.

4. The system of claim 1, further comprising:

a vacuum pump, coupled to the processor, operable to evacuate the chamber.

5. The system of claim 4, wherein the processor is further configured to:

cause the vacuum pump to evacuate the chamber to remove at least a portion of the alcohol.

6. The system of claim 1, wherein the processor is further configured to:

cause the sterilization process to be aborted.

7. A sterilization process, executable by a sterilizer, for sterilizing a medical device positioned in a chamber of the sterilizer, comprising:

detecting, based on one or more parameters of the sterilization process executed on the sterilizer, alcohol on or in the medical device, monitoring a plasma power profile of the sterilization process, and detecting the alcohol based on a characteristic of the plasma power profile; and in response to the alcohol being detected, running a routine to remove at least a part of the alcohol on or in the medical device.

8. The sterilization process of claim 7, wherein the detecting step comprises:

monitoring a degradation rate of hydrogen peroxide vapor; and detecting the alcohol based on a comparison of the degradation rate and an expected degradation curve.

9. The sterilization process of claim 7, wherein the running step comprises:

evacuating the chamber of the sterilizer to remove at least a portion of the alcohol.

10. The sterilization process of claim 7, wherein the running step comprises:

extinguishing plasma in the chamber of the sterilizer;

evacuating the chamber; and reactivating plasma in the chamber.

11. The sterilization process of claim 7, wherein the running step comprises:

circulating air through the chamber of the sterilizer or over the medical device for a predetermined period.

12. The sterilization process of claim 7, wherein the running step comprises:

aborting the sterilization process to enable at least a portion of the alcohol to be removed outside of the chamber of the sterilizer.

13. The sterilization process of claim 7, wherein the one or more parameters comprise an evacuation time to achieve a target plasma pressure; and wherein the running step comprises:

aborting the sterilization process in response to (i) the plasma power profile being erratic or (ii) the evacuation time exceeding a threshold.

14. A system for sterilization, comprising:

a chamber operable to receive a device to be sterilized;

a processor operable to drive a sterilization process and further configured to:

detect, based on one or more parameters of the sterilization process, alcohol on or in the device; and in response to the alcohol being detected, run a routine to remove at least a part of the alcohol on or in the device; and a hydrogen peroxide sensor, coupled to the processor, operable to detect levels of hydrogen peroxide within the chamber, wherein the one or more parameters comprise a degradation rate of the hydrogen peroxide within the chamber, and wherein the processor is further configured to:

detect the alcohol based on a comparison of the degradation rate of the hydrogen peroxide within the chamber and an expected degradation curve.

15. The system of claim 14, further comprising:

a plasma generator, coupled to the processor, operable to generate a plasma in the chamber.

16. The system of claim 15, wherein the one or more parameters comprise a plasma power profile associated with generating the plasma, and wherein the processor is further configured to:

detect the alcohol based on a characteristic of the plasma power profile associated with generating the plasma.

17. The system of claim 14, further comprising:

a vacuum pump, coupled to the processor, operable to evacuate the chamber.

18. The system of claim 17, wherein the processor is further configured to:

cause the vacuum pump to evacuate the chamber to remove at least a portion of the alcohol.

19. The system of claim 14, wherein the processor is further configured to:

cause the sterilization process to be aborted.

* * * * *